United States Patent
Thomson et al.

(10) Patent No.: US 8,067,728 B2
(45) Date of Patent: Nov. 29, 2011

(54) METHOD OF IMPROVING SIGNAL-TO-NOISE FOR QUANTITATION BY MASS SPECTROMETRY

(75) Inventors: Bruce A. Thomson, Toronto (CA); Yves Le Blanc, Newmarket (CA)

(73) Assignee: DH Technologies Development Pte. Ltd., Singapore (SG)

( * ) Notice: Subject to any disclaimer, the term of this patent is extended or adjusted under 35 U.S.C. 154(b) by 729 days.

(21) Appl. No.: 12/035,499

(22) Filed: Feb. 22, 2008

(65) Prior Publication Data
US 2009/0212205 A1 Aug. 27, 2009

(51) Int. Cl.
*B01D 59/44* (2006.01)
*H01J 49/00* (2006.01)

(52) U.S. Cl. ........... 250/282; 250/281; 250/288; 702/23

(58) Field of Classification Search .................. 250/281, 250/282, 288
See application file for complete search history.

(56) References Cited

U.S. PATENT DOCUMENTS

| | | | | |
|---|---|---|---|---|
| 5,939,612 | A * | 8/1999 | Wylie et al. | 73/23.36 |
| 6,940,065 | B2 | 9/2005 | Graber et al. | |
| 7,279,679 | B2 * | 10/2007 | Old et al. | 250/282 |
| 7,473,892 | B2 * | 1/2009 | Sano et al. | 250/281 |
| 2001/0027382 | A1 * | 10/2001 | Jarman et al. | 702/179 |
| 2002/0024010 | A1 | 2/2002 | Hager et al. | |
| 2004/0181351 | A1 * | 9/2004 | Thompson et al. | 702/76 |
| 2005/0206363 | A1 * | 9/2005 | Ho et al. | 324/76.22 |
| 2005/0261838 | A1 * | 11/2005 | Andreev et al. | 702/22 |
| 2006/0255258 | A1 * | 11/2006 | Wang et al. | 250/282 |
| 2006/0284067 | A1 * | 12/2006 | Senko et al. | 250/282 |
| 2006/0284069 | A1 * | 12/2006 | Le Blanc | 250/282 |
| 2007/0023633 | A1 * | 2/2007 | Wang et al. | 250/282 |

(Continued)

FOREIGN PATENT DOCUMENTS
WO WO/94/09698 A1 5/1994

OTHER PUBLICATIONS

Gomez et al., "Solid-phase extraction followed by liquid chromatography-time-of-flight-mass spectrometry to evaluate pharmaceuticals in effluents. A pilot monitoring study", Journal of Environmental Monitoring, 2007, 9, pp. 718-729.*

(Continued)

*Primary Examiner* — Robert Kim
*Assistant Examiner* — Michael J Logie
(74) *Attorney, Agent, or Firm* — John R. Kasha; Kasha Law LLC

(57) ABSTRACT

Selectivity of a measurement from a mass spectrometer is improved by selecting an extracted ion current window for the measurement after data acquisition. A plurality of mass spectra are acquired over a period of time. A first extracted ion current window is selected and from the plurality of mass spectra a first intensity as a function of time is calculated for an ion using the first extracted ion current window. A second extracted ion current window is selected and from the plurality of mass spectra a second intensity as a function of time is calculated for the ion using the second extracted ion current window. A first signal-to-noise ratio of the first intensity is compared with a second signal-to-noise ratio of the second intensity. If the second signal-to-noise ratio is greater than the first signal-to-noise ratio, the second intensity as a function of time is used for the measurement.

22 Claims, 14 Drawing Sheets

U.S. PATENT DOCUMENTS

| | | | |
|---|---|---|---|
| 2008/0015793 A1* | 1/2008 | Ben-Menahem et al. | 702/30 |
| 2008/0015821 A1* | 1/2008 | Roushall | 702/191 |
| 2008/0149821 A1* | 6/2008 | Senko | 250/282 |
| 2008/0234945 A1* | 9/2008 | Walk et al. | 702/19 |
| 2009/0166224 A1* | 7/2009 | Yang et al. | 205/792 |
| 2010/0136703 A1* | 6/2010 | Purkayastha | 436/124 |
| 2010/0163721 A1* | 7/2010 | Graves et al. | 250/282 |

OTHER PUBLICATIONS

Borges et al. "Analysis of a Challenging Subset of World Anti-Doping Agency-Banned Steroids and Antiestrogens by LC-MS-MS" Journal of Analytical Toxicology, vol. 31, Apr. 2007, pp. 125-131.*

* cited by examiner

| Product Ion (m/z) | Concentration (pico-grams) | Intensity (ions) |
|---|---|---|
| 59 | 0.25 to 100 | 10 to 4000 |
| 89 | 0.1 to 40 | 10 to 4000 |
| 122 | 10 to 4000 | 10 to 4000 |
| 231 | 30 to 4000 | 10 to 1333 |
| 269 | 0.05 to 20 | 10 to 4000 |

| Product Ion (m/z) | Sample Intensity (ions) |
|---|---|
| 59 | 5500 |
| 89 | 7500 |
| 122 | 128 |
| 231 | 45 |
| 269 | 8300 |

1400

METHOD OF IMPROVING SIGNAL-TO-NOISE FOR QUANTITATION BY MASS SPECTROMETRY

INTRODUCTION

Quantitation by mass spectrometry is conventionally performed with a triple-quadrupole mass spectrometer using a multiple reaction monitoring (MRM) method that selects certain product and precursor ion combinations to provide the best signal-to-noise ratio (S/N). The product and precursor ion combinations must be selected before acquisition. As a result, matrix interferences can limit the S/N that can be achieved.

DRAWINGS

The skilled person in the art will understand that the drawings, described below, are for illustration purposes only. The drawings are not intended to limit the scope of the applicant's teachings in any way.

FIG. 13 is a table showing the linear ranges of the calibration curves of five product ions of an exemplary known compound, in accordance with the present teachings.

Figure 1:
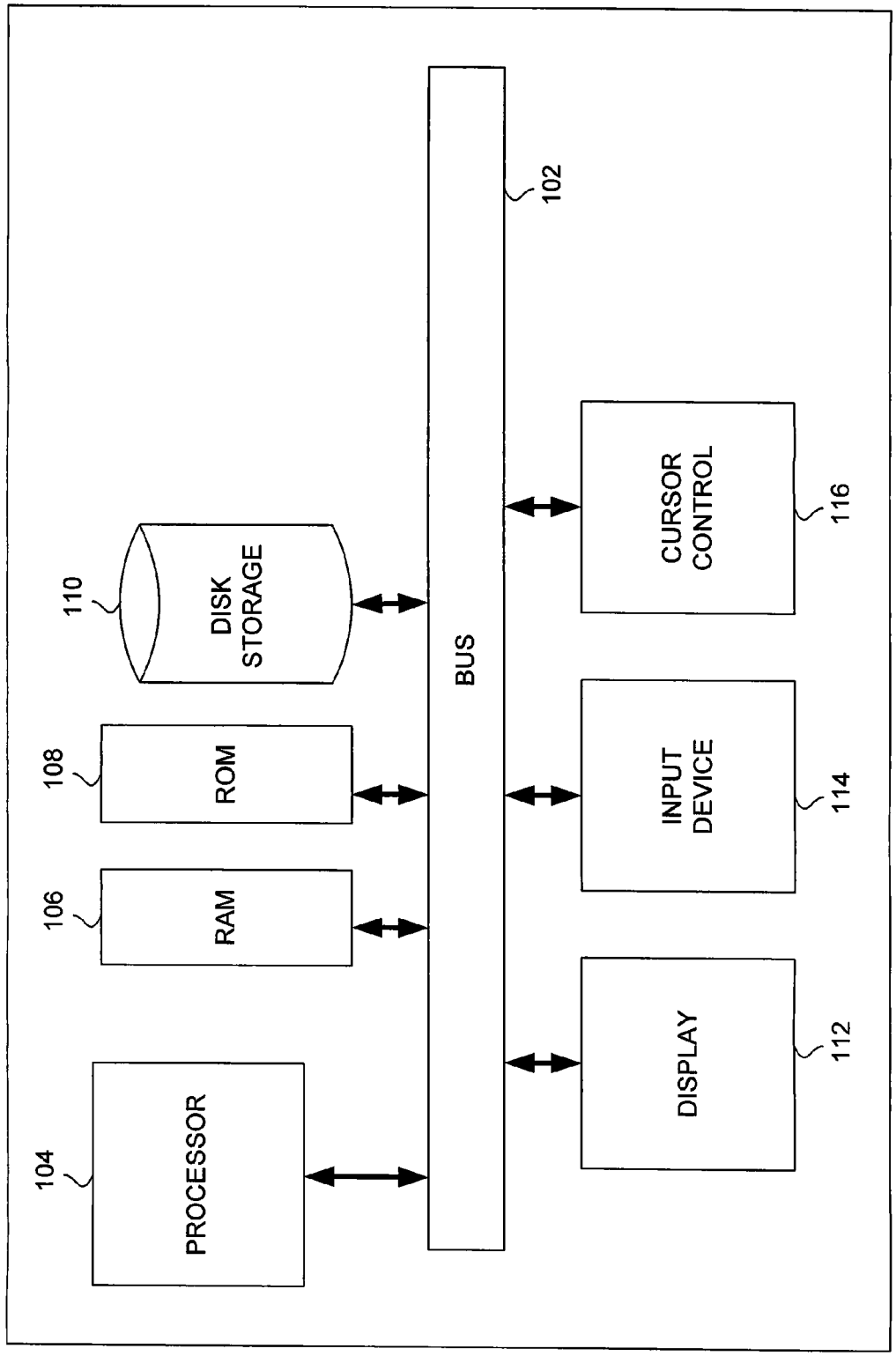
FIG. 1 is a block diagram that illustrates a computer system, upon which embodiments of the present teachings may be implemented.

Before one or more embodiments of the invention are described in detail, one skilled in the art will appreciate that the invention is not limited in its application to the details of construction, the arrangements of components, and the arrangement of steps set forth in the following detailed description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF VARIOUS EMBODIMENTS

The section headings used herein are for organizational purposes only and are not to be construed as limiting the subject matter described in any way.

Computer Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for determining base calls, and instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane.

Computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium can include, but is not limited to, a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Methods of Data Processing

Selectivity

Triple quadrupole mass spectrometers are widely used to measure the amount or concentration of compounds such as, for example, pharmaceuticals in plasma or urine samples. A precursor and product ion combination must be selected in advance when using the multiple reaction monitoring (MRM) method with a triple quadrupole mass spectrometer. Additionally, with a triple quadrupole, the mass resolution (peak width) must be tuned and fixed in advance of the data acquisition. It is not possible after the acquisition to change or select the width of the XIC window with a triple quadrupole.

In contrast, when a triple-quadrupole mass spectrometer with a time-of-flight mass spectrometer replacing the third quadrupole (QqTOF) is used for quantitation, a product ion or multiple product ions can be selected after acquisition of a sample spectrum. There is no need to characterize the matrix or select the best MRM combinations in advance. There is no need to perform these steps in advance because a QqTOF spectrometer can obtain a full product ion spectrum.

The measurement of a concentration of an amount of a known compound in a sample is often performed, for example, by acquiring mass spectra continuously during a time period in which the sample elutes from a liquid chromatograph (LC) column. Alternatively, the compound can be injected into a flowing liquid stream without an LC column, in a technique called flow injection analysis (FIA). Spectra are acquired continuously during a time period, which can be of several minutes in duration, commonly with a frequency of 1 spectrum per second. In various embodiments, a plurality of spectra acquired during this time period forms a data set which can be processed by calculating an extracted ion current (XIC) for each ion of interest.

Also, in various embodiments the mass-to-charge width, or width of the XIC window, for each product ion can be selected after the acquisition of a plurality of sample spectra to provide the best signal-to-noise ratio (S/N). For example, a narrow XIC window that corresponds to less than the width of the mass peak can be selected for processing if there is an improvement in the S/N compared to selecting a wider XIC window. Both the center position and the width of the selected window can be selected to provide maximum signal-to-noise. For example, the center of the XIC window can be chosen to be on one side of the actual mass value if there is an interfering mass peak that overlaps on the other side of the mass peak of interest. In order to generate a measurable signal, the selected XIC window must overlap to some degree with the position of the true mass peak of interest. In various embodiments the selection of the width of the XIC window is selected after the acquisition of the plurality of sample spectra, avoiding the necessity of tuning the mass spectrometer for a specific mass resolution before the analysis.

Figure 2:
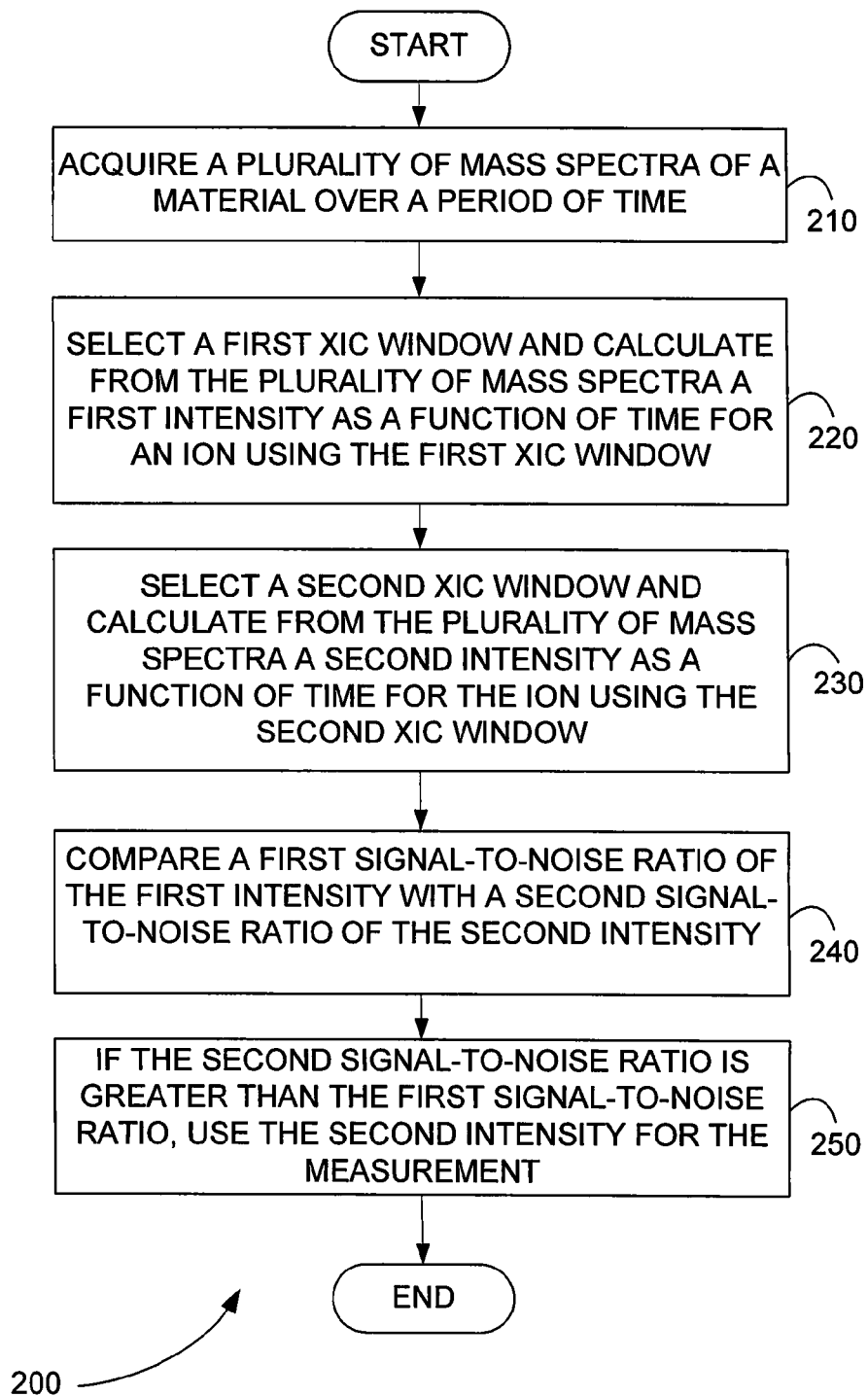
FIG. 2 is a flowchart showing a method for improving selectivity of a measurement from a mass spectrometer, in accordance with the present teachings.

FIG. 2 is a flowchart showing a method 200 for improving selectivity of a measurement from a mass spectrometer, in accordance with the present teachings. The mass spectrometer can include, but is not limited to, a time of flight mass spectrometer or an electrospray ionization time of flight mass spectrometer. The measurement can be, for example, a quantitation measurement.

In step 210 of method 200, a plurality of mass spectra of a material are acquired over a period of time. The plurality of mass spectra can be, for example, product ion mass spectra.

In step 220, a first XIC window is selected and from the plurality of mass spectra a first intensity as a function of time is calculated for an ion using the first XIC window. The first XIC window includes a first width and a first center, for example. The ion can be, for example, a product ion. The first XIC window is selected after acquisition of the plurality of mass spectra, for example.

In step 230, a second XIC window is selected and from the plurality of mass spectra a second intensity as a function of time is calculated for the ion using the second XIC window. The second XIC window includes a second width and a second center, for example. The second XIC window is selected after acquisition of the plurality of mass spectra, for example.

In step 240, a first S/N of the first intensity is compared with a second S/N of the second intensity.

In step 250, if the second S/N is greater than the first S/N, the second intensity as a function of time is used for the measurement.

In various embodiments, the first width is larger than the second width. In various embodiments, the first width and the width have values less than 0.02 atomic mass units. In various embodiments, the first center and the second center are not equal.

Figure 3:
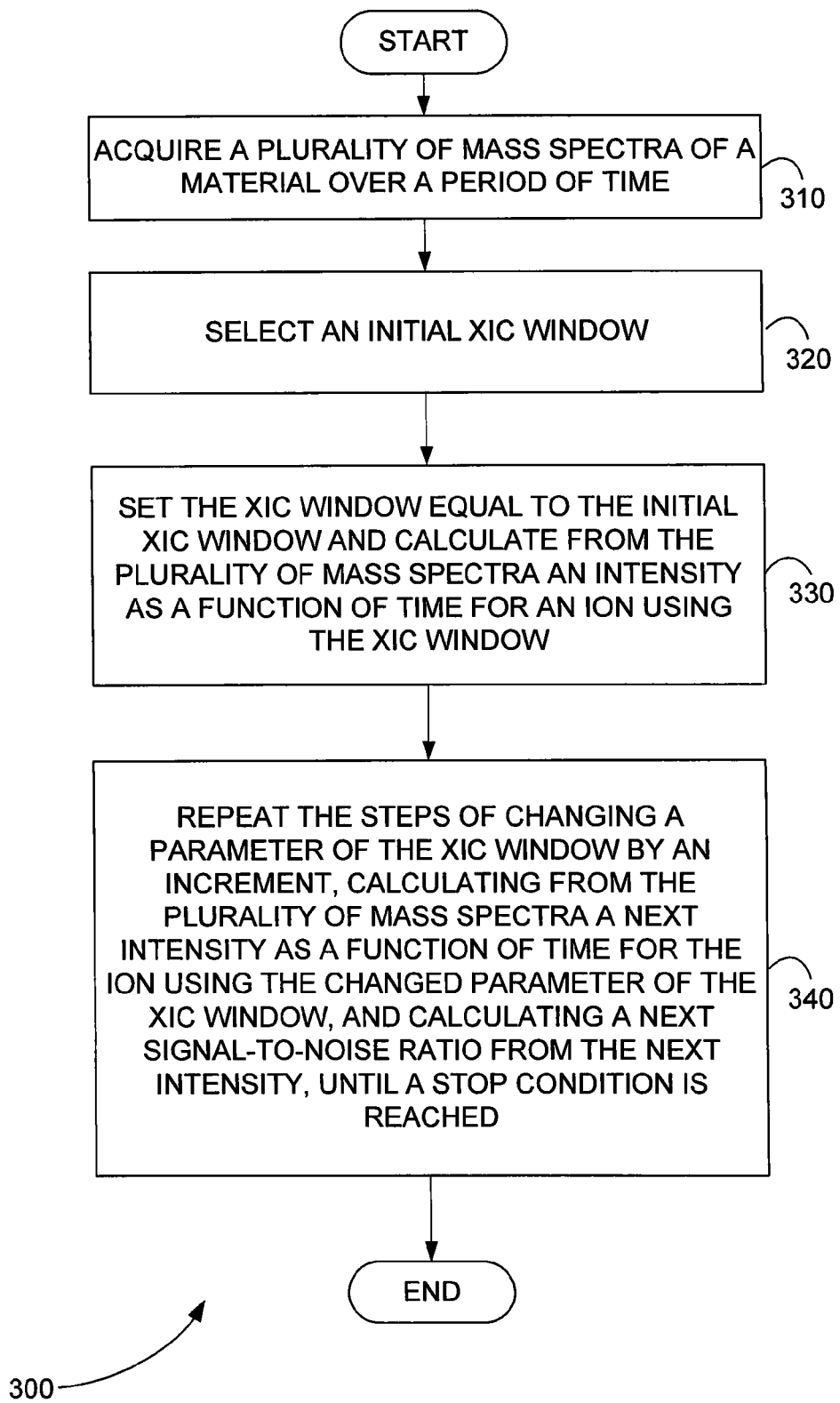
FIG. 3 is a flowchart showing a method for determining an extracted ion current (XIC) window to use for a mass spectrometer measurement, in accordance with the present teachings.

FIG. 3 is a flowchart showing a method 300 for determining an XIC window to use for a mass spectrometer measurement, in accordance with the present teachings. The mass spectrometer can include, but is not limited to, a time of flight mass spectrometer or an electrospray ionization time of flight mass spectrometer. The measurement can be, for example, a quantitation measurement.

In step 310 of method 300, a plurality of mass spectra of a material are acquired over a period of time. The plurality of mass spectra can be, for example, product ion mass spectra.

In step 320, an initial XIC window is selected. The initial XIC window can be selected after acquisition of the plurality of mass spectra.

In step 330, the XIC window is set equal to the initial XIC window and from the plurality of mass spectra an intensity as a function of time is calculated for an ion using the XIC window. The ion can be, for example, a product ion.

In step 340, the steps of changing a parameter of the XIC window by an increment, calculating from the plurality of mass spectra a next intensity as a function of time for the ion using the changed parameter of the XIC window, and calculating a next S/N from the next intensity are repeated until a stop condition is reached. The stop condition is, for example, the next S/N reaching a maximum S/N. The XIC window at the maximum S/N can then be used for the measurement.

In various embodiments, the stop condition is the next S/N becoming greater than or equal to a threshold. The threshold can be, for example, 3. A parameter of the XIC window includes, but is not limited to, the width or the center. Changing a parameter of the XIC window by an increment can include, but is not limited to, decreasing the parameter by the increment or increasing the parameter by the increment. The increment can be, for example, 0.01 atomic units.

Figure 4:
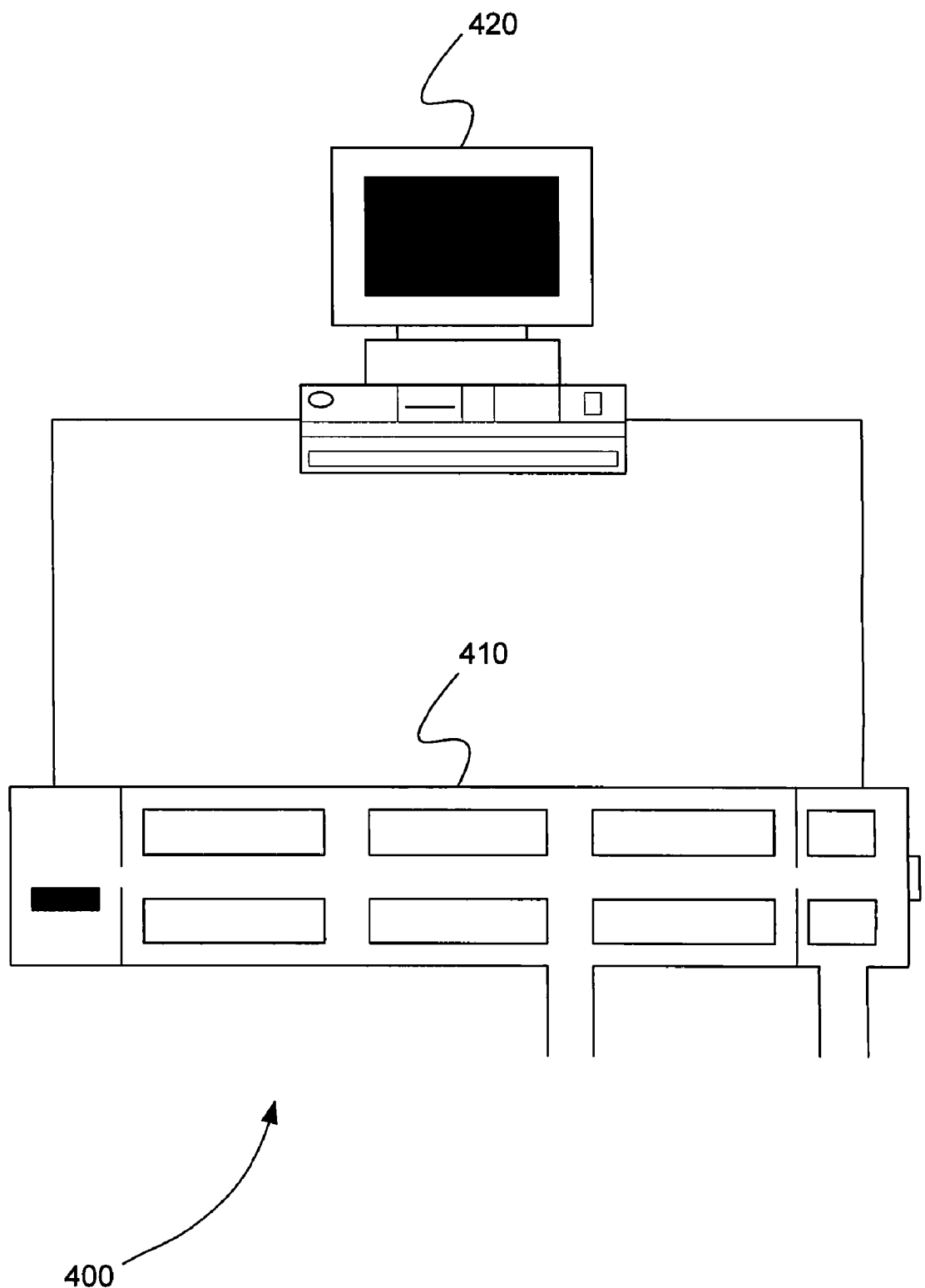
FIG. 4 is a schematic diagram of a mass spectrometry system that includes a mass spectrometer and computer system, in accordance with the present teachings.

FIG. 4 is a schematic diagram of a mass spectrometry system 400 that includes a mass spectrometer 410 and a computer system 420, in accordance with the present teachings. Mass spectrometer 410 can include, but is not limited to, a time-of-flight mass spectrometer or an electrospray ionization time of flight mass spectrometer.

Computer system 420 is in communication with mass spectrometer 410. Computer system 420 can be, but is not limited to, computer system 100, shown in FIG. 1 and described above. Computer system 420 acquires a plurality of mass spectra of a material over a period of time, selects a first XIC window and calculates from the plurality of mass spectra a first intensity as a function of time for an ion using the first XIC window, selects a second XIC window and calculates from the plurality of mass spectra a second intensity as a function of time for the ion using the second XIC window, compares a first S/N of the first intensity with a second S/N of the second intensity, and, if the second S/N is greater than the first S/N, uses the second intensity as a function of time for the measurement. Computer system 420 can select the first XIC window and the second XIC window after acquisition of the plurality of mass spectra, for example.

Quantitation

When a triple-quadrupole mass spectrometer with a time-of-flight mass spectrometer replacing the third quadrupole (QqTOF) is used for quantitation, a full product ion spectrum can be obtained. The spectrum can include a range of product ions, some more intense than others. In various embodiments, a wide dynamic range can be obtained by using the most intense product ions for quantitation at low concentrations, and using less intense product ions for quantitation at high concentration where the larger-intensity ions are saturated.

This wide dynamic range is possible with a QqTOF mass spectrometer, because the intensities of less intense ions are not affected by the intensities of the more intense ions. Use of a QqTOF mass spectrometer also allows a product ion or multiple product ions to be selected for quantitation after acquisition of a sample spectrum. In contrast, the use of a conventional triple-quadrupole spectrometer using a multiple reaction monitoring (MRM) method requires that a product ion or multiple product ions be selected for quantitation before a sample is analyzed. Additionally, with a triple quadrupole, the mass resolution (peak width) must be tuned and fixed in advance of the data acquisition. It is not possible after the acquisition to change or select the width of the extracted ion current (XIC) window with a triple quadrupole.

Using a QqTOF mass spectrometer, a range of linear response for each product ion can be established from a calibration curve, and multiple product ions can be used to produce a linear calibration curve over a wide range of concentrations. An internal standard can be used to compensate for matrix and ionization suppression effects.

Other mass spectrometers can also be used to provide a full product ion spectrum and wide dynamic range. These spectrometers include, but are not limited to, a linear ion trap mass spectrometer, an orbitrap mass spectrometer, a Fourier transform mass spectrometer, or a three-dimensional ion trap mass spectrometer.

In various embodiments, calibration curves are constructed for more than one production of the same precursor, the acquired product ion spectra of a sample is processed, and the concentration of the sample is measured by selecting the product ion or product ions that are still in the linear portion of the response curve. Multiple product ions can be used for the measurement of concentration by combining the measurements in an algorithm that assigns confidence or precision based on statistical criteria. For example, two product ions can be used to measure the concentration, but if the signal-to-noise ratio (S/N) of one product ion is much lower than the other, then the two results can be combined in a statistically relevant method. A statistically relevant method can include, but is not limited to, weighting the two results based on their S/Ns.

In various embodiments, a method of using a mass spectrometer for quantitative measurement of an unknown concentration can include producing a response curve from a standard material over a wide range of concentrations, where full product ion spectra are acquired over the range of concentrations, measuring the linearity of response for at least two product ions with different responses, and measuring the response to an unknown sample concentration by acquiring the product ions spectrum, and determining the concentration from the intensity of the product ions that corresponds to a linear portion of the response curve.

Figure 5:
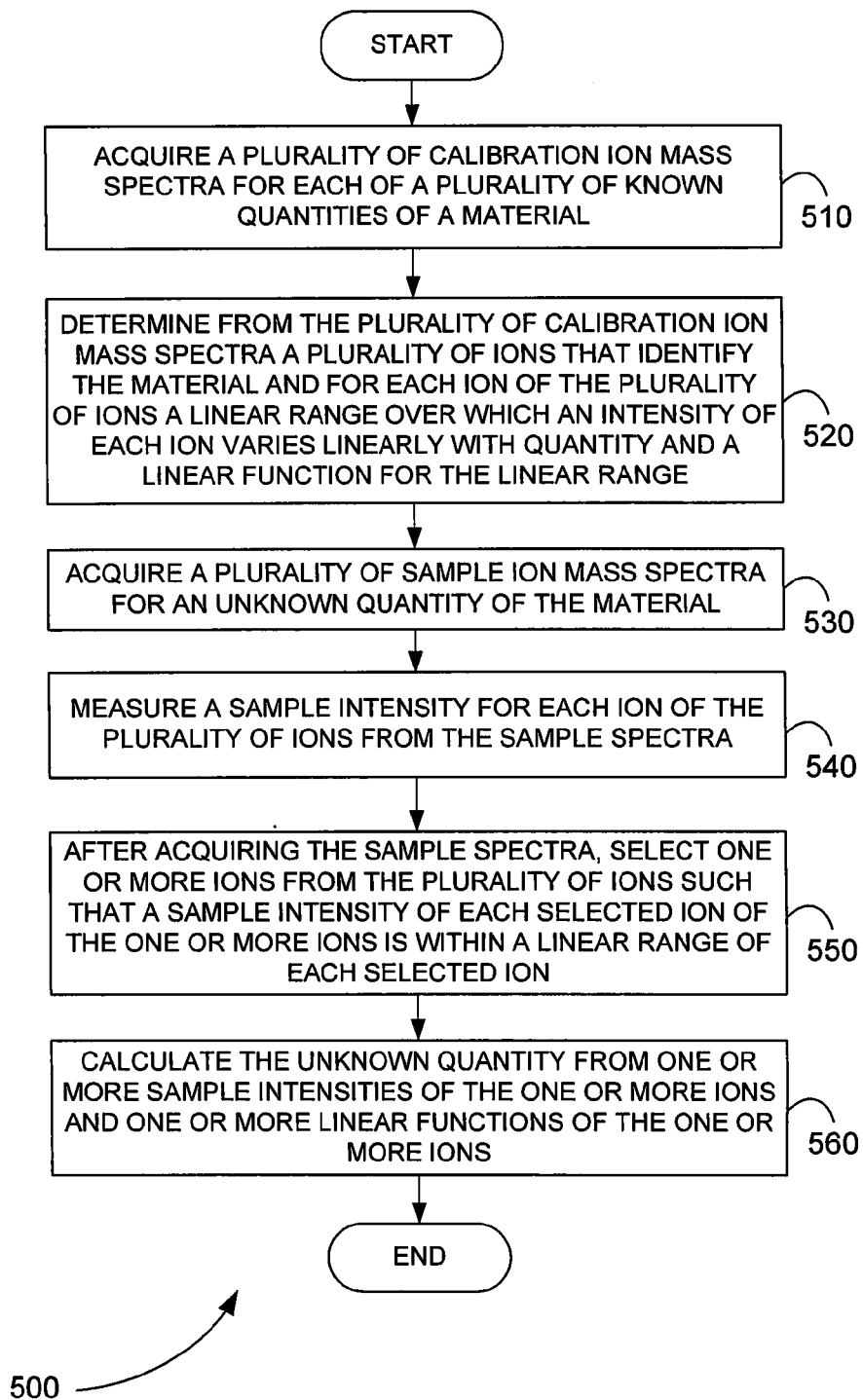
FIG. 5 is a flowchart showing a method for quantitation using data from a mass spectrometer, in accordance with the present teachings.

FIG. 5 is a flowchart showing a method 500 for quantitation using data from a mass spectrometer and involving the selection two or more ions within their linear ranges, in accordance with the present teachings. The mass spectrometer can include, but is not limited to, a time-of-flight mass spectrometer, a linear ion trap mass spectrometer, an orbitrap mass spectrometer, a Fourier transform mass spectrometer, or a three-dimensional ion trap mass spectrometer.

In step 510 of method 500, a plurality of calibration ion mass spectra are acquired for each of a plurality of known quantities of a material. The plurality of calibration ion mass spectra is, for example, a plurality of product ion mass spectra.

In step 520, from the plurality of calibration ion mass spectra a plurality of ions that identify the material is determined and for each ion of the plurality of ions a linear range over which an intensity of each ion varies linearly with quantity and a linear function for the linear range are determined.

In step 530, a plurality of sample ion mass spectra is acquired for an unknown quantity of the material. A sample ion mass spectrum is, for example, a product ion mass spectrum. In various embodiments, the resolution of a quadrupole mass filter can be adjusted to transmit a mass window that includes two or more isotopes of the compound. It is common that carbon-13 containing isotopes provide precursor ions of less intensity than the first isotope. Selection of a mass window that includes two or more isotopes of the precursor ion can result in product ions that contain carbon-13 isotopes and are less intense than the first isotope. These less intense product ions can be used for quantitation. Alternatively, the unfragmented precursor ion and its isotopes can be used for quantitation. Alternatively, quantitation can be done in a time-of-flight mass spectrometry (TOFMS) mode using the precursor ion and its isotopes to provide a range of ion intensities. In various embodiments, quantitation can be done in a TOFMS system using product ions that are created without selecting the precursor ions, for example, by fragmentation in the ion source, in the declustering region, or in the ion optics region before the time-of-flight (TOF).

In step 540, a sample intensity is measured for each ion of the plurality of ions from the sample spectra.

In step 550, after acquiring the sample spectra, one or more ions from the plurality of ions are selected such that a sample intensity of each selected ion of the one or more ions is within a linear range of each selected ion. In various embodiments, the one or more ions are selected only if the signal to noise ratio of each ion of the one or more ions is greater than or equal to a threshold value. A S/N threshold value is 3, for example. Signal-to-noise can be determined by methods that are known in the art. For example, signal-to-noise can be determined by calculating the ratio of the peak height to the standard deviation of the background ion signal in a selected time window. Other measurements of signal-to-noise can also be used.

In step 560, the unknown quantity is calculated from one or more sample intensities of the one or more ions and one or more linear functions of the one or more ions. In various embodiments, the one or more ions can include two or more ions. In various embodiments, calculating the unknown quantity can include averaging two or more quantities of the two or more ions, where each quantity of the two or more quantities is obtained from a sample intensity and a linear function of an ion of the two or more ions. In various embodiments, calculating the unknown quantity can also include summing two or more weighted quantities of the two or more ions, wherein each weighted quantity of the two or more weighted quantities is obtained from a signal-to-noise weighting factor, a sample intensity, and a linear function of an ion of the two or more ions.

In various embodiments, a sample intensity is measured by measuring the extracted ion current (XIC) as a function of time, and determining the area under a curve that corresponds to a time window that is characteristic of the sample compound. For example, the characteristic window can be the time window in which the compound elutes from a liquid chromatography system. The XIC is a measurement of intensity consisting of the sum or integral of the ion current measurement within a fixed mass-to-charge window in the mass spectrum. For example, a mass peak of a product ion has a characteristic mass peak width that is determined by the resolution of the mass spectrometer. It is common to select an XIC window width that corresponds to all or a major portion of the mass peak, and to select a center value for the XIC window that consists of the known mass value (which can be the peak top or centroid of the mass peak). In some cases the XIC can consist of a single mass peak point, corresponding to the minimum width of the mass scale. This minimum width in a time-of-flight mass spectrometer is the minimum time resolution or bin size of the time measurement. The intensity of the minimum width peak can also be the same as the peak height in the mass spectrum.

Also, in various embodiments the width of the XIC window for each product ion can be selected after the acquisition of a sample spectrum to provide the best signal-to-noise ratio (S/N). For example, a narrow XIC window that corresponds to less than the width of the mass peak can be selected for processing if there is an improvement in the S/N compared to selecting a wider XIC window. Both the center position and the width of the selected window can be selected to provide maximum signal-to-noise. For example, the center of the XIC window can be chosen to be on one side of the actual mass value if there is an interfering mass peak that overlaps on the other side of the mass peak of interest. In order to generate a measurable signal, the selected XIC window must overlap to some degree with the position of the true mass peak of interest.

In various embodiments, the width and position of the XIC window for each mass in the spectrum known to be associated with the compound of interest is selected in order to provide a maximum S/N. The XIC window width can be different for each selected mass value. For each mass value, the XIC window width selected to provide a maximum S/N can be used to calculate a concentration from a calibration curve that is generated from the calibration samples by using the same XIC window width. For example, if m/z 255.035 is a sample mass and an XIC window width of 0.015 atomic mass units (amu) provides the best S/N for a particular known sample of unknown concentration, then the concentration can be calculated from a calibration curve for m/z 255.035 that uses the same width of 0.015 amu for the XIC. The calibration curves of a different XIC window width can be generated by the computer before the samples of unknown concentration are run or after the samples are run.

Also in various embodiments, the position of the XIC window can be selected to provide the best S/N. For example, if the known exact m/z of the sample ion is 255.035, then the XIC window for m/z 255.035 with a width of 0.015 amu can be selected by the computer, and the S/N of the peak at the correct retention time can be calculated. Next, the XIC window for m/z 255.045 can be calculated with a width of 0.015 amu. If the S/N for a peak at the correct retention time is higher for m/z 255.045 than for m/z 255.035, then this XIC window can be used to measure the sample concentration from the calibration curve.

In various embodiments, after acquiring the sample spectrum, one or more ions are selected from the plurality of ions. For each selected ion the best XIC window width can be determined by measuring the S/N for a range of XIC window widths. For each selected mass value, a calibration curve can be generated for the selected XIC window width from calibration data. One or more ions can be selected from the plurality of ions such that a sample intensity of each selected ion of the one or more ions is within a linear range of the calibration curve of each selected ion.

In various embodiments, the center position of the XIC window can be selected in order to provide the best S/N.

In various embodiments, a first XIC window and a second XIC window for at least one of the one or more ions are selected. The first XIC window width of the first XIC window is not equal to a second XIC window width of the second XIC window, for example. In various embodiments, a first XIC window center position of the first XIC window is not equal to a second XIC window center position of the second XIC window. A first sample intensity for the at least one of the one or more ions is calculated using the first XIC window and a second sample intensity for the at least one of the one or more ions is calculate using the second XIC window. A first S/N of the first sample intensity is calculated and a second S/N of the second sample intensity is calculated. If the second S/N is greater than the first S/N, the second sample intensity is used to calculate the unknown quantity.

In various embodiments, a first XIC window and a second XIC window for at least one of the one or more ions are selected. The first XIC window width of the first XIC window is not equal to a second XIC window width of the second XIC window, for example. In various embodiments, a first XIC window center position of the first XIC window is not equal to a second XIC window center position of the second XIC window. A first sample intensity for the at least one of the one or more ions is calculated using the first XIC window and a second sample intensity for the at least one of the one or more ions is calculated using the second XIC window. A first relative contribution of a closely eluting compound in the sample to the first sample intensity is calculated and a second relative contribution of the closely eluting compound in the sample to the second sample intensity is calculated. A relative contribution of a closely eluting compound in the sample to the sample intensity is a measure of interference between the closely eluting compound in the sample and the material of interest in the compound. The relative contribution of the closely eluting compound in the sample to the sample intensity is, for example, the proportion of the sample intensity due to the closely eluting compound relative to the proportion of the sample intensity due to the materiel of interest. If the second relative contribution is less than the first relative contribution; the second sample intensity is used to calculate the unknown quantity.

The linear range of the calibration curve, in terms of sample concentration or sample amount for each of the known ions in the sample, is not dependent on the width of the XIC window selected for the calibration. For example, if the linear range of calibration for the ion of m/z 255.035 is from 10 femto-grams (fg) to 10 pico-grams (pg) as determined from a calibration curve with an XIC window width of 0.02 amu, then the linear range of the calibration curve for an XIC window width of 0.01 amu will still be from 10 fg to 10 pg. For any ion mass, the linear range for any selected XIC window width will all be the same. This is because the non-linearity or curvature at the upper end of the range is due to saturation of the ion detector, which is caused by the number of ions in the entire mass peak hitting the detector at that particular sample concentration. Therefore the range of linearity in sample concentration is determined by the number if ions in the mass peak. Selecting a different XIC window width changes the number of ion counts associated with the sample concentration, and therefore changes the absolute intensity value of the calibration curve, but does not change the shape of the calibration curve.

In various embodiments, an XIC window width can be selected for each of the known ions of the sample. Calibration curves can be determined for each of the known ions, and linear ranges determined for each of the known ions. For each unknown sample, the response for each known ion can be determined by using the XIC window width. The ions that have a response within the linear range can be determined. For those ions that are within the linear response range, the XIC window width and center value can be varied and selected according to the methods described above in order to determine the best XIC window width. If a different XIC window width or center value is selected than that used for the calibration curve for that ion, a new calibration curve can be calculated by using the new selected XIC window width, and the concentration of the sample can be calculated based on the new calibration curve. The improved S/N obtained from the new selected XIC window can provide a more accurate measurement of the sample concentration than was obtained from the original XIC window width.

In various embodiments the best XIC window can be selected before the linear range of the calibration is determined. After finding the best XIC window for each ion, the calibration curve can be produced by using that XIC window to process the data from the plurality of calibration ion mass spectra. For each ion and selected XIC window the linear range of response and a linear function can be determined. The unknown quantity is calculated from one or more sample intensities of the one or more ions and one or more linear functions of the one or more ions.

In various embodiments, a mass spectrometry system includes mass spectrometer and computer system. The mass spectrometer can include, but is not limited to, a time-of-flight mass spectrometer, a linear ion trap mass spectrometer, an orbitrap mass spectrometer, a Fourier transform mass spectrometer, or a three-dimensional ion trap mass spectrometer.

The computer system is in communication with mass spectrometer. The computer system can be, but is not limited to, computer system 100, shown in FIG. 1 and described above. The computer system acquires a plurality of calibration ion mass spectra for each of a plurality of known quantities of a material, determines from the plurality of calibration ion mass spectra a plurality of ions that identify the material and for each ion of the plurality of ions a linear range over which an intensity of each ion varies linearly with quantity and a linear function for the linear range, acquires a plurality of sample ion mass spectra for an unknown quantity of the material, measures a sample intensity for each ion of the plurality of ions from the sample spectra, after acquiring the sample spectra, selects one or more ions from the plurality of ions such that a sample intensity of each selected ion of the one or more ions is within a linear range of each selected ion, and calculates the unknown quantity from one or more sample intensities of the one or more ions and one or more linear functions of the one or more ions. In various embodiments, the width and center position of the XIC window is selected for each of the plurality of ions before the one or more ions is selected such that the sample intensity is within the linear range of the calibration curve.

EXAMPLES

Aspects of the applicant's teachings may be further understood in light of the following examples, which should not be construed as limiting the scope of the present teachings in any way.

Selectivity

Figure 6:
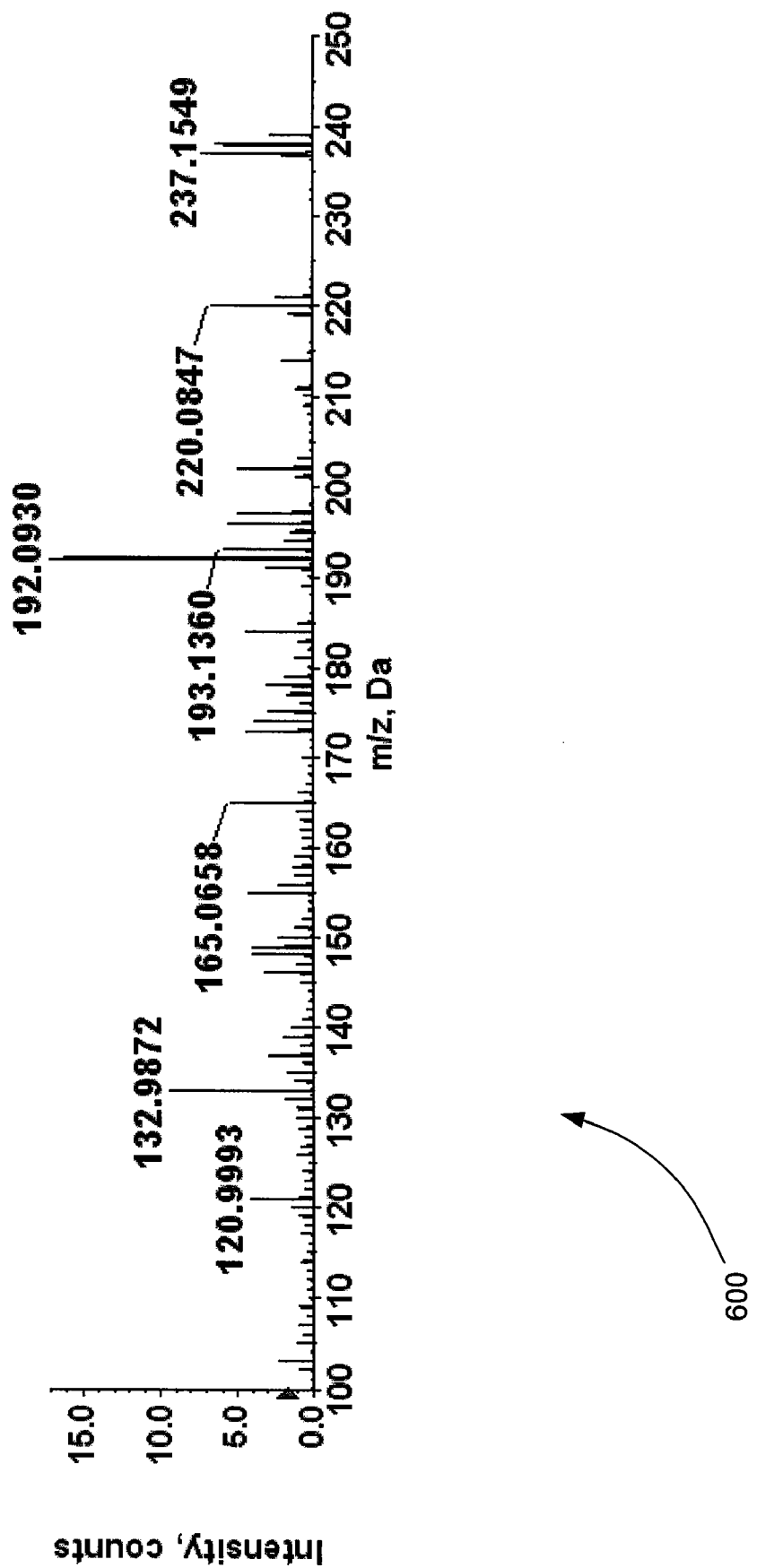
FIG. 6 is an exemplary product ion mass spectrum from a urine sample, in accordance with the present teachings.

FIG. 6 is an exemplary product ion mass spectrum 600 from a urine sample, in accordance with the present teachings. Spectrum 600 is a product ion spectrum of a precursor with mass-to-charge ratio (m/z) 237. Many peaks are present, but only a few are associated with the drug of interest (Carbamazepine).

Figure 7:
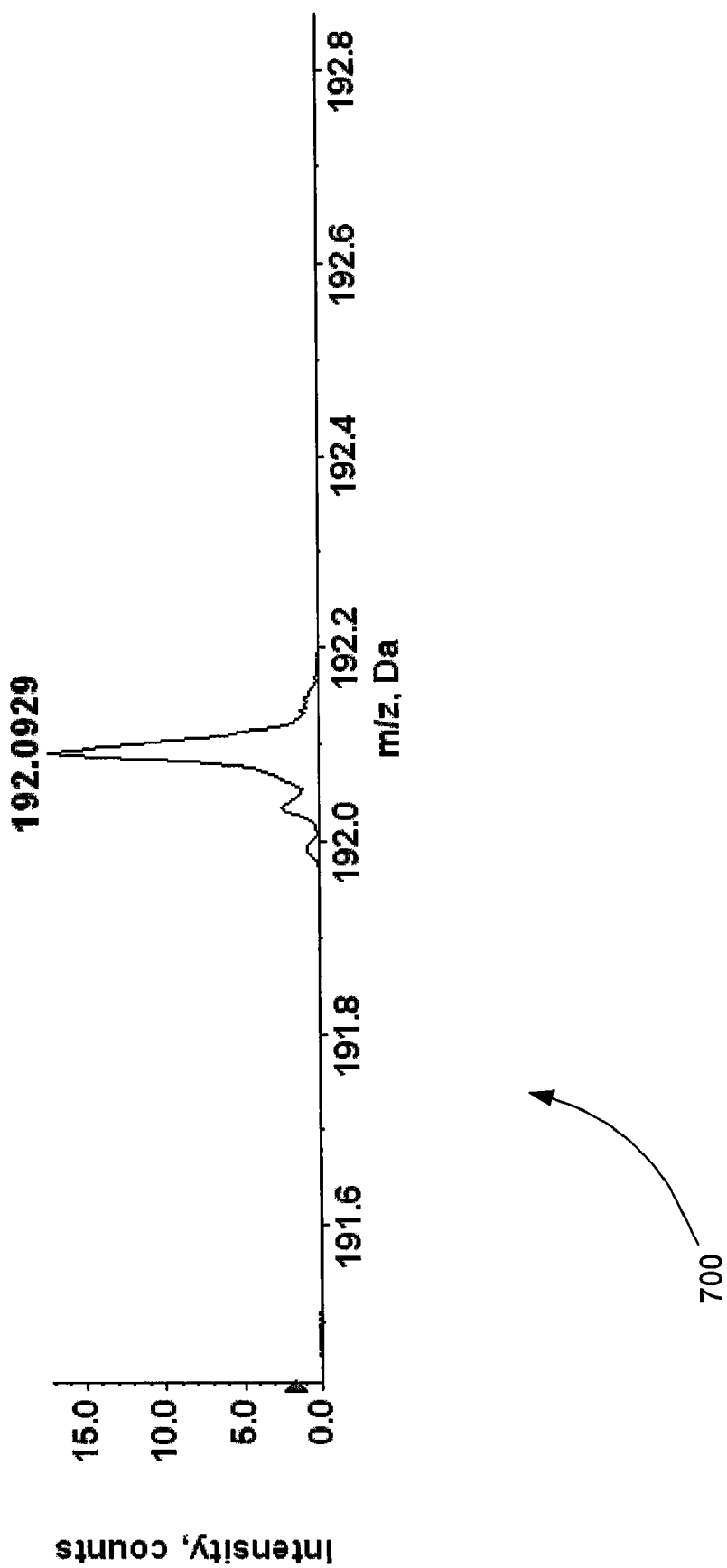
FIG. 7 is an exemplary expanded view of a product ion mass spectrum from a urine sample, in accordance with the present teachings

FIG. 7 is an exemplary expanded view of a product ion mass spectrum 700 from a urine sample, in accordance with the present teachings. Spectrum 700 shows that even at m/z 192 product mass, there are several components present. Only 192.0929, however, is due to Carbamazapine.

Figure 8:
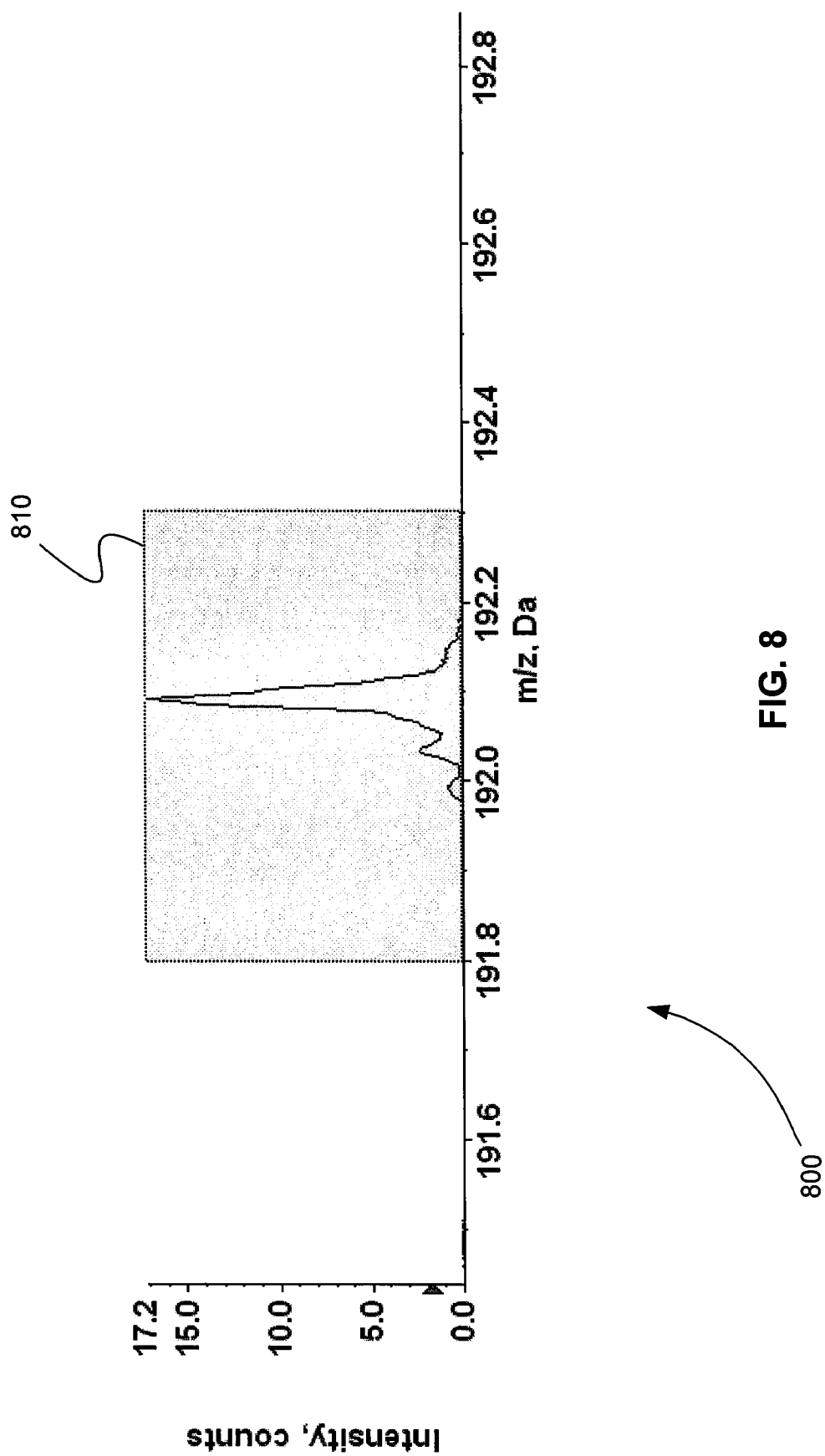
FIG. 8 is an exemplary expanded view of a product ion mass spectrum from a urine sample showing an XIC window with a width of 0.5 atomic mass units (amu), in accordance with the present teachings.

FIG. 8 is an exemplary expanded view of a product ion mass spectrum 800 from a urine sample showing an extracted ion current (XIC) window 810 with a width of 0.5 atomic mass units (amu), in accordance with the present teachings. Selected XIC window 810 extends from 191.799 to 192.305 Daltons (Da) and has a center at 192.052 Da. Selected XIC window 810 includes all components at m/z 192 product mass.

Figure 9:
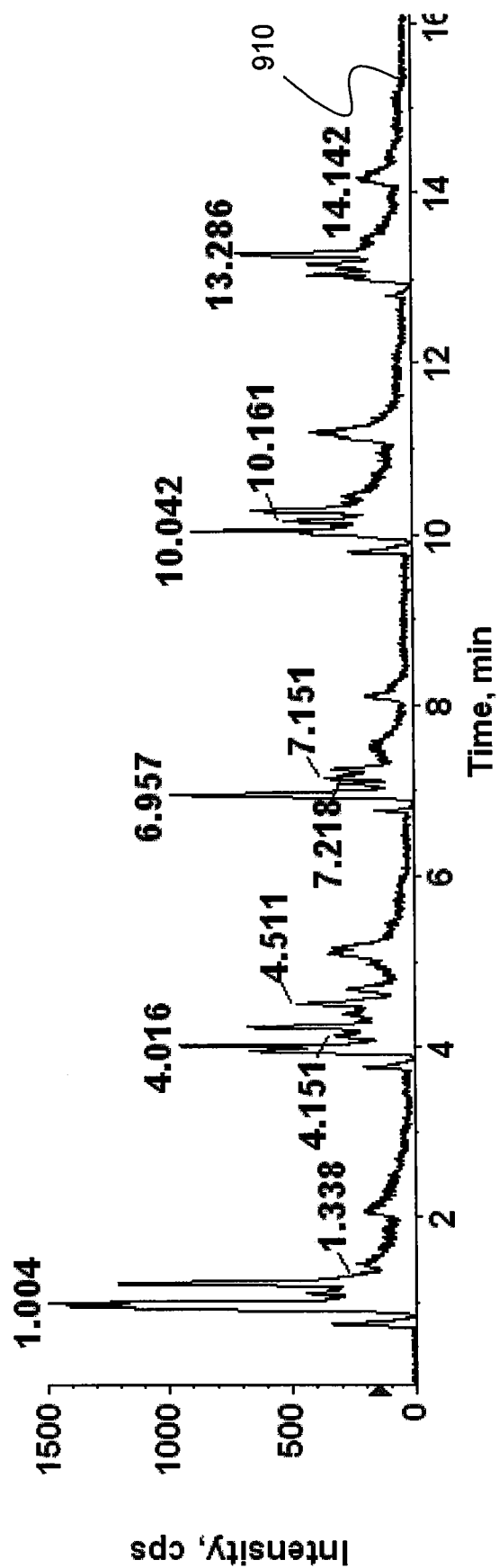
FIG. 9 is an exemplary plot of the XIC for five samples injected about three minutes apart using the XIC window shown in FIG. 8, in accordance with the present teachings.

FIG. 9 is an exemplary plot 900 of the XIC 910 for five samples injected about three minutes apart using XIC window 810 shown in FIG. 8, in accordance with the present teachings. Each sample is slightly different and has multiple peaks. Only one peak is Carbamazapine. The other peaks are potential interferences that are separated by liquid chromatography (LC) in this case, but might not be in other cases.

Figure 10:
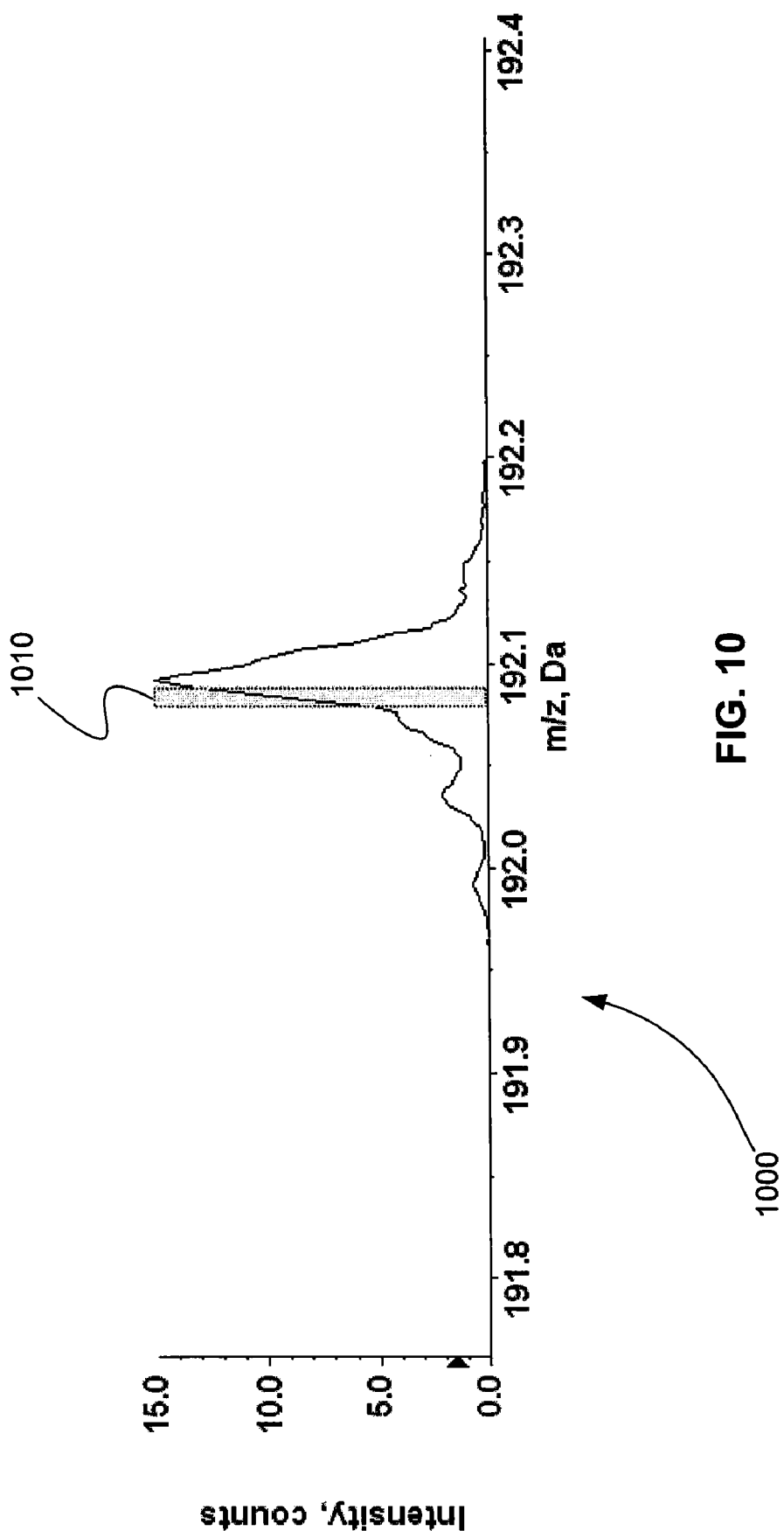
FIG. 10 is an exemplary expanded view of a product ion mass spectrum from a urine sample showing an XIC window with a width of 0.01 amu, in accordance with the present teachings.

FIG. 10 is an exemplary expanded view of a product ion mass spectrum 1000 from a urine sample showing an XIC window 1010 with a width of 0.01 atomic mass units (amu), in accordance with the present teachings. FIG. 10 shows the same data as shown in FIG. 8, but now using a narrower XIC window. Selected XIC window 1010 extends from 192.079 to 192.089 Da and has a center at 192.084 Da. Selected XIC window 1010 does not include all of the components at m/z 192 product mass.

Figure 11:
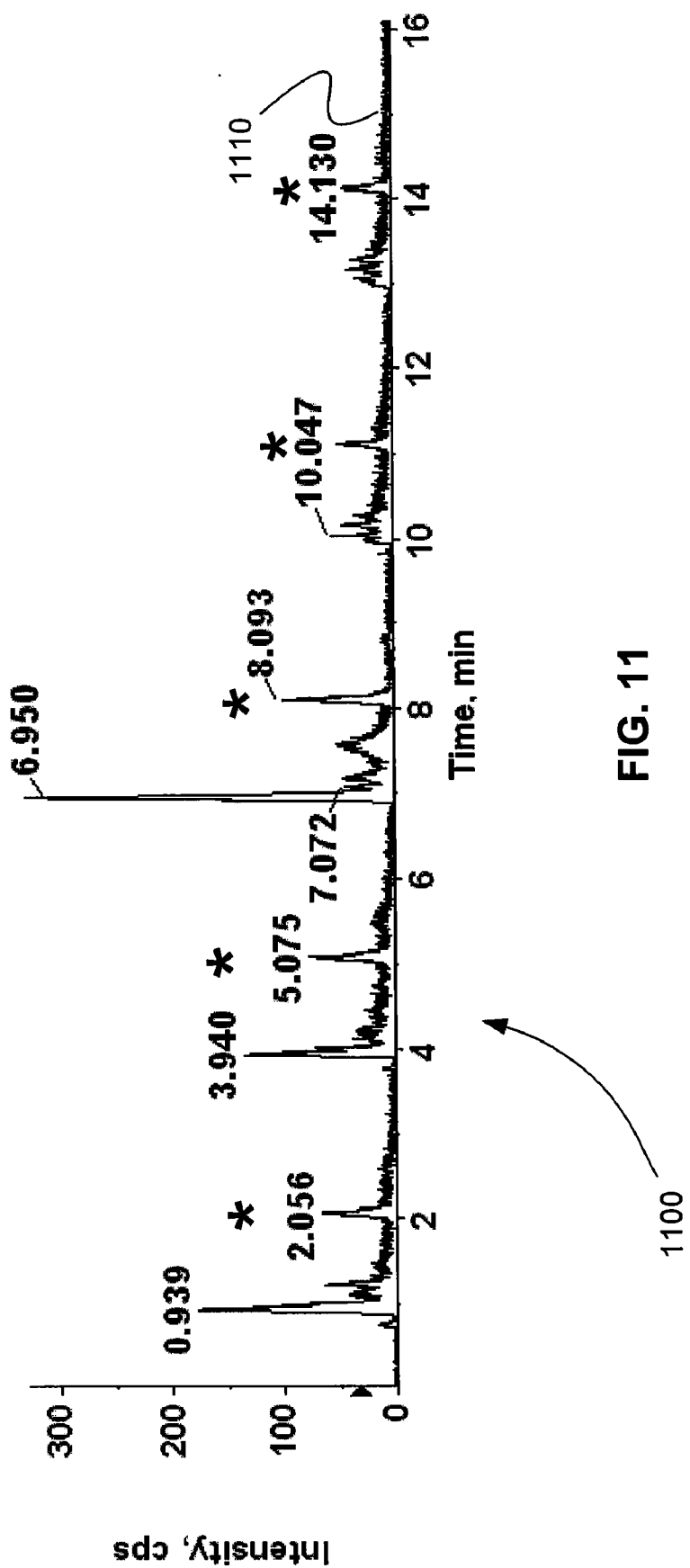
FIG. 11 is an exemplary plot of the XIC for five samples injected about three minutes apart using the XIC window shown in FIG. 10, in accordance with the present teachings.

FIG. 11 is an exemplary plot 1100 of the XIC 1110 for five samples injected about three minutes apart using the XIC window shown in FIG. 10, in accordance with the present teachings. Comparing FIG. 11 with FIG. 9 shows that selected narrower XIC window 1010, shown in FIG. 10 and centered at 192.084 Da, provides a better S/N than selected XIC window 810, shown in FIG. 8 and centered at 192.052 Da. The width and center of XIC window 1010, shown in FIG. 10, and the width and center of XIC window 810, shown in FIG. 8, are, for example, chosen after sample data acquisition and selected so that each XIC window includes or is near correct mass value for Carbamazepine. The correct mass value is known from a standard, for example.

Figure 12:
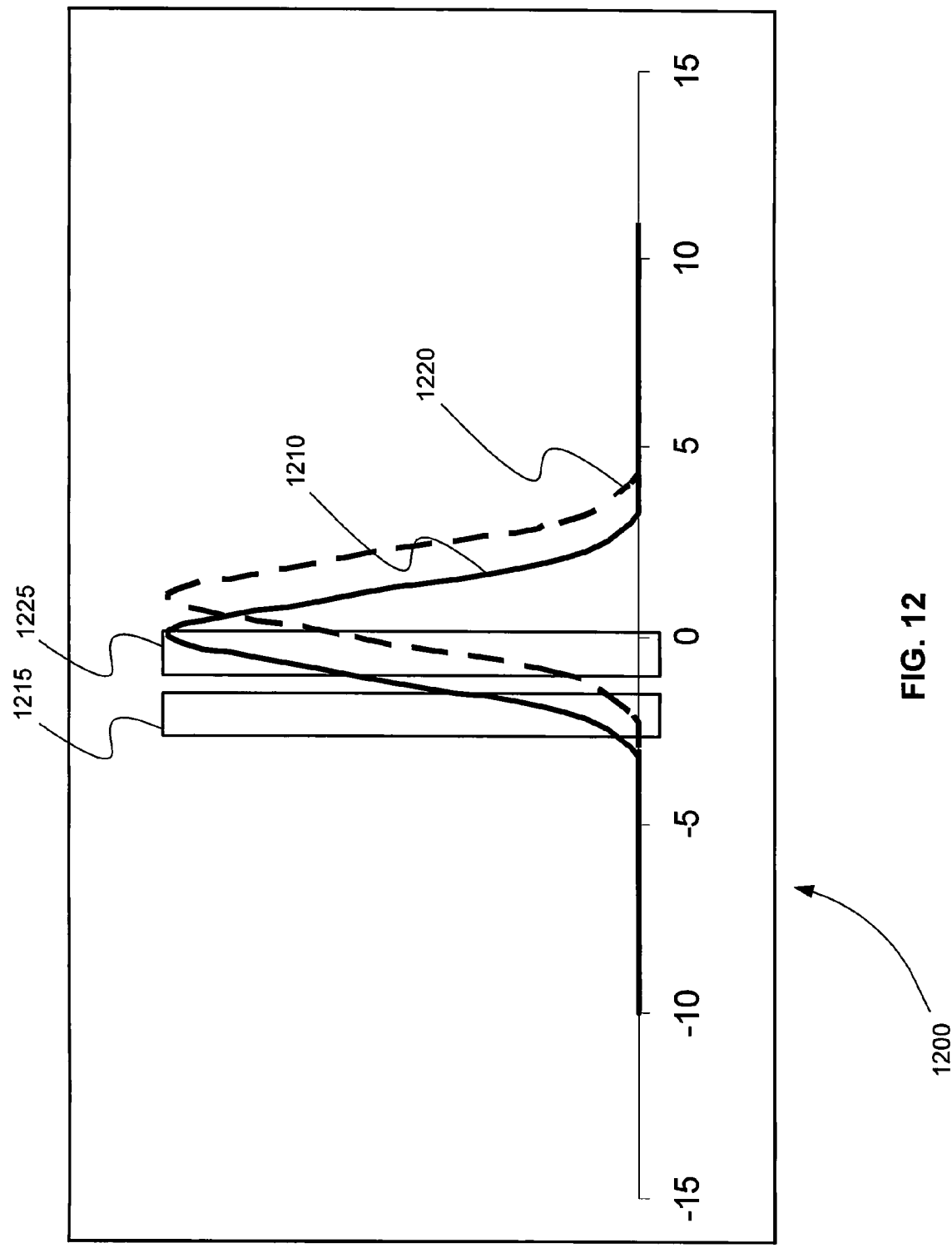
FIG. 12 is an exemplary plot of a mass peak of interest and an interfering mass peak, showing how it can be advantageous to select a position of the XIC window that is not centered on the true center of the mass of interest, in accordance with the present teachings.

FIG. 12 is an exemplary plot 1200 of a mass peak of interest 1210 and an interfering mass peak 1220, showing how it can be advantageous to select a position of the XIC window that is not centered on the true center of the mass of interest, in accordance with the present teachings. If XIC window 1225 is selected, the XIC will contain significant contributions from both mass peak of interest 1210 and interfering mass peak 1220. If XIC window 1215 is selected, the signal from mass peak of interest 1210 is reduced, but the signal from interfering mass peak 1220 is reduced even more, so the S/N is increased.

Quantitation

According to an exemplary method for quantitation using data from a mass spectrometer a series of standards are run over a range of concentrations. From the series of standards, a calibration curve is constructed for each product ion over the entire range of concentrations. For each calibration curve, the highest concentrations are discarded until a linear function is regression fit to the curve within a threshold value. A threshold value for linearity can be determined from a coefficient of determination $R^2 > 0.995$ where R is the coefficient of variations, determined using standard and well-known regression methods, for example. In various embodiments, the threshold value can be greater than or less than 0.995.

Alternatively, other criteria can be used to determine where the calibration function becomes non-linear. For example, a threshold value can be used below which the deviation from linearity is acceptable, and above which the deviation from linearity is unacceptable. In various embodiments a weighted linear regression may be used. In one example of weighted linear regression, a weighting factor of 1/x is applied to each data point where x is the sample concentration. Weighted linear regression is known in the art.

As a result, a linear calibration curve that covers a certain range of concentrations is obtained for each ion. These calibration curves are generated and stored prior to running unknown samples. In various embodiments, the calibration curves can be obtained after running the unknown samples and before processing the data to determine the concentrations of the unknowns. In various embodiments, calibration curves can be run before an unknown sample and after running an unknown sample, and two or more calibration curves can be combined in a statistically reasonable fashion, for example by averaging the calibration curves together.

After running a sample, the response for each of the known product ions in the sample is measured. The intensity of each product ion in the sample is then compared with its calibration curve to determine if the intensity is within the linear range of that calibration curve. If the intensity is within the linear range, the product ion can be used for quantitation.

Consider an exemplary known compound with a precursor mass-to-charge ratio (m/z) of 287 and product ions with m/z's of 59, 89, 122, 231, and 269. Using the method described above, the linear ranges of the calibrations curves for each of the product ions can be found and shown in terms of concentration and intensity.

FIG. 13 is a table 1300 showing the linear ranges of the calibration curves of five product ions of the exemplary known compound, in accordance with the present teachings. The data shown in table 1300 is consistent with a mass spectrometer that saturates (or becomes non-linear) above 4000 ions and has a detection limit of 10 ions.

Figure 14:
FIG. 14 is a table showing the intensities of five product ions of an exemplary known compound that are found in a sample, in accordance with the present teachings.

Again using the method described above, a sample is run and the response for each of the known product ions in the sample is measured. FIG. 14 is a table 1400 showing the intensities of five product ions of an exemplary known compound that are found in the sample, in accordance with the present teachings. Table 600 shows that product ions with m/z's 59, 89, and 269 are outside of the linear calibration ranges for those ions. Therefore the concentration of the known compound in the sample is calculated from the concentrations of the product ions with m/z 122 (128 ions=128 pico-grams (pg)) and m/z 231 (45 ions=135 pg). The concentration of the known compound can be found from the concentrations of the two product ions, for example. The concentration of the known compound can also be found by combining the concentrations of the two product ions in a statistically significant fashion.

An exemplary statistically significant method of combining the concentrations of the two product ions includes averaging the two concentrations together, or in various embodiments by using a weighting factor based on the relative signal-to-noise ratios (S/N's) of the two sample intensity measurements. For example, if the S/N of m/z 122 is measured as 6 and the S/N of m/z 231 is measured as 20, then the calculated concentration is 128 multiplied by 6/26 plus 135 multiplied by 20/26, or 133.3 pg.

In another exemplary method, a known compound has a precursor mass-to-charge ratio (m/z) of 287 and product ions with m/z's of 59, 89, 122, 231, and 269. The exemplary known compound has known exact m/z values of 287.135 for the precursor ion and 59.035, 89.088, 122.103, 231.145 and 269.201 for the product ions. The analysis of the known compound at unknown concentrations in complex biological samples can be made difficult by the presence of interfering compounds with the same or very similar precursor ion mass and the same or very similar product ion masses. For example, an exemplary interfering compound has a precursor ion mass 287.155 with a plurality of product ions, one of which is product ion of m/z 122.113. The interfering precursor ion can be transmitted through the quadrupole mass filter even when it is set to transmit the sample ion mass of m/z 287.135 because the quadrupole mass filter resolution can only separate ions that differ in mass by approximately 0.7 amu. A time-of-flight mass spectrometer with a mass resolution of 10,000 at half-height can partly but not fully separate the mass value of 122.103 from the sample and 122.113 from the interfering compound. If the interfering compound elutes from the LC column very close in time to the sample compound, the interfering compound can interfere with the measurement of the sample. If the XIC window center value is 122.103, and the XIC window width is 0.02 amu, then the XIC window will include the integral of the ion signal between m/z 122.093 and 122.113. If the interfering compounds are slightly separated by the LC, then two peaks can be observed in the chromatogram and the calculation of sample concentration will be difficult due to the second peak in the chromatogram. If the interfering compound comprises a background ion signal that is constant in time, then the XIC of the sample ion will appear as a signal that is sitting on top of the constant background signal from the interfering ion. This will result in reduced S/N for the sample measurement. If the XIC window is reduced to 0.01 amu, then the XIC will comprise the integral of the ion signal from m/z 122.098 to 122.108, and a significant portion of the interfering ion signal from m/z 122.113 will be eliminated. This will improve the S/N and the ability to identify the area of the peak in the LC chromatogram. After selecting the XIC window width of 0.01 amu, a calibration curve for the known compound can be measured from the calibration data by using an XIC window width of 0.01 amu for the calibration data, and the linear range of the calibration curve can be determined using the methods described above. The unknown concentration of the sample can be determined by the intensity of the 122 peak with the selected XIC window width if it falls within the linear range of the calibration curve. In other embodiments, the XIC window width for other product ions in the sample spectrum can be selected by using this method, and the concentration of the sample determined by combining the measurements from linear calibration curves by using statistical methods described above.

While the applicants' teachings are described in conjunction with various embodiments, it is not intended that the applicants' teachings be limited to such embodiments. On the contrary, the applicants' teachings encompass various alternatives, modifications, and equivalents, as will be appreciated by those of skill in the art.

For example, the range of linearity for a known ion can be selected by determining the ratio of adjacent isotopic peaks, and determining when this ratio changes by an amount that indicates that the larger peak is saturating. Alternatively, a predetermined ion count can be chosen as a threshold value beyond which the response of the detector is not linear. In various embodiments only those ions with XIC or peak intensities that are less than this threshold value can be selected for quantitation. The threshold value can be specified to depend on the XIC window width selected.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A method for improving selectivity of a measurement from a mass spectrometer, comprising:
    acquiring a plurality of mass spectra of a material over a period of time;
    selecting a first extracted ion current window and calculating from the plurality of mass spectra a first intensity as a function of time for an ion using the first extracted ion current window;
    selecting a second extracted ion current window and calculating from the plurality of mass spectra a second intensity as a function of time for the ion using the second extracted ion current window, wherein the first extracted ion current window comprises a first center position, the second extracted ion current window comprises a second center position, and the first center position is not equal to the second center position;
    comparing a first signal-to-noise ratio of the first intensity with a second signal-to-noise ratio of the second intensity; and
    if the second signal-to-noise ratio is greater than the first signal-to-noise ratio, using the second intensity for the measurement.

2. The method of claim 1,
    wherein the plurality of mass spectra comprise a product ion spectrum and the ion comprises a product ion of a multiple reaction monitoring experiment.

3. The method of claim 1, wherein the first extracted ion current window and the second extracted ion current window are selected after the acquisition of the plurality of mass spectra.

4. The method of claim 1, wherein the first extracted ion current window comprises a first width and the second extracted ion current window comprises a second width.

5. The method of claim 4, wherein the first width is larger than the second width.

6. The method of claim 4, wherein the first width comprises a value less than 0.02 atomic mass units.

7. The method of claim 4, wherein the second width comprises a value less than 0.02 atomic mass units.

8. The method of claim 1, wherein the measurement comprises quantitation.

9. A method for determining an extracted ion current window to use for a mass spectrometer measurement, comprising:
    acquiring a plurality of mass spectra of a material over a period of time;
    selecting an initial extracted ion current window;
    setting the extracted ion current window equal to the initial extracted ion current window and calculating from the plurality of mass spectra an intensity as a function of time for an ion using the extracted ion current window; and repeating steps comprising:
  changing a parameter of the extracted ion current window by an increment, wherein the parameter comprises a center position,
  calculating from the plurality of mass spectra a next intensity as a function of time for the ion using the parameter, and
  calculating a next signal-to-noise ratio from the next intensity, until a stop condition is reached.

10. The method of claim 9, wherein the stop condition comprises the next signal-to-noise ratio reaching a maximum signal-to-noise ratio.

11. The method of claim 9, wherein the stop condition comprises the next signal-to-noise ratio becoming greater than or equal to a threshold.

12. The method of claim 9, further comprising repeating the step of changing a second parameter of the extracted ion current window by a second increment, wherein the second parameter comprises a width until the stop condition is reached.

13. The method of claim 9, wherein changing the parameter of the extracted ion current window by the increment comprises decreasing the parameter of the extracted ion current window by the increment.

14. The method of claim 9, wherein changing the parameter of the extracted ion current window by the increment comprises increasing the parameter of the extracted ion current window by the increment.

15. The method of claim 9, wherein the initial extract ion current window is selected after acquisition of the plurality of mass spectra.

16. The method of claim 9, wherein the increment comprises 0.01 atomic mass units.

17. A mass spectrometry system, comprising:
a mass spectrometer; and
a computer system in communication with the mass spectrometer that:
  acquires a plurality of mass spectra of a material over a period of time;
  selects a first extracted ion current window and calculates from the plurality of mass spectra a first intensity as a function of time for an ion using the first extracted ion current window;
  selects a second extracted ion current window and calculates from the plurality of mass spectra a second intensity as a function of time for the ion using the second extracted ion current window, wherein the first extracted ion current window comprises a first center position, the second extracted ion current window comprises a second center position, and the first center position is not equal to the second center position;
  compares a first signal-to-noise ratio of the first intensity with a second signal-to-noise ratio of the second intensity; and
  if the second signal-to-noise ratio is greater than the first signal-to-noise ratio, uses the second intensity for the measurement.

18. The mass spectrometry system of claim 17, wherein the computer system selects the first extracted ion current window and the second extracted ion current window after the acquisition of the plurality of mass spectra.

19. The mass spectrometry system of claim 17, wherein the mass spectrometer comprises a time of flight mass spectrometer.

20. The mass spectrometry system of claim 17, wherein the spectrometer comprises an electrospray ionization time of flight mass spectrometer.

21. A computer-readable medium whose contents cause a processor to perform a method for improving selectivity of a measurement from a mass spectrometer, the contents comprising:
  acquiring a plurality of mass spectra of a material over a period of time;
  selecting a first extracted ion current window and calculating from the plurality of mass spectra a first intensity as a function of time for an ion using the first extracted ion current window;
  selecting a second extracted ion current window and calculating from the plurality of mass spectra a second intensity as a function of time for the ion using the second extracted ion current window, wherein the first extracted ion current window comprises a first center position, the second extracted ion current window comprises a second center position, and the first center position is not equal to the second center position;
  comparing a first signal-to-noise ratio of the first intensity with a second signal-to-noise ratio of the second intensity; and
  if the second signal-to-noise ratio is greater than the first signal-to-noise ratio, using the second intensity for the measurement.

22. The computer-readable medium of claim 21, wherein the first extracted ion current window and the second extracted ion current window are selected after the acquisition of the plurality of mass spectra.

* * * * *